United States Patent [19]

De Fraguier et al.

[11] Patent Number: 5,774,960
[45] Date of Patent: Jul. 7, 1998

[54] PROCESS FOR MANUFACTURING A MULTI-ELEMENT ACOUSTIC PROBE, ESPECIALLY AN ECHOGRAPH PROBE

[75] Inventors: Sixte De Fraguier, Antibes; Jean-François Gelly, Valbonne; Jean-Marc Bureau, Bures sur Yvette, all of France

[73] Assignee: Thomson-CSF, Paris, France

[21] Appl. No.: 507,304

[22] PCT Filed: Mar. 4, 1994

[86] PCT No.: PCT/FR94/00237

§ 371 Date: Aug. 29, 1995

§ 102(e) Date: Aug. 29, 1995

[30] Foreign Application Priority Data

Mar. 5, 1993 [FR] France .................. 93 02586

[51] Int. Cl.⁶ .................................................. H01L 41/22
[52] U.S. Cl. .................................. 29/25.35; 310/336
[58] Field of Search ................ 29/25.35; 310/334–337

[56] References Cited

U.S. PATENT DOCUMENTS

| 4,747,192 | 5/1988 | Rokurota | 29/25.35 |
| 5,091,893 | 2/1992 | Smith et al. | 29/25.35 X |

*Primary Examiner*—Carl E. Hall
*Attorney, Agent, or Firm*—Oblon, Spivak, McClelland, Maier & Neustadt, P.C.

[57] ABSTRACT

A process relating to the manufacture of medical echograph probes for establishing a network of connections to elementary transducer units. The process includes the steps of cutting transducer units from a piezoelectric plate, drilling holes in a polymer film on the piezoelectric plate by means of a photoablation process or a reactive ion plasma etching process, and making connections by metallization and then etching to form conducting tracks which connect to the piezoelectric layer via the drilled holes.

12 Claims, 7 Drawing Sheets

PROCESS FOR MANUFACTURING A MULTI-ELEMENT ACOUSTIC PROBE, ESPECIALLY AN ECHOGRAPH PROBE

The present invention relates to manufacturing processes which can be used to obtain acoustic probes comprising a set of transmitter and/or receiver elements obtained by cutting from a large-sized transducer block. It essentially relates to the means which can be used to make the electrical connections between these elements and the electronic devices which are connected to them. It makes it possible to facilitate the manufacture of transducers which include a large number of elements arranged in a two-dimensional arrangement. It also applies to one-dimensional arrangements, since these are easier to produce than the two-dimensional arrangements.

In order to obtain a beam of acoustic waves, that is directed and focused as required, from an electroacoustic transducer equipping an echograph probe, this transducer is generally divided into a set of elements supplied by signals suitably phase-shifted or staggered over time. This set of elements is generally obtained by cutting a block of transducer material, and the electrical signals applied to these elements are brought in via a set of connections made by various means. The most widely-used probes comprise a set of elements placed in a one-dimensional alignment. The connections to these elements are then taken off, either laterally or in the top and bottom planes of the block of piezoelectric ceramic from which the elements have been cut. A description of such a probe will, for example, be found in the French patent filed on 28 Nov., 1986 under No. 86/16660 and published on 3 Jun., 1988 under No. 2,607,590. Since these planes are continuous, it is only necessary to establish a single connection and the available area is large.

Such a one-dimensional arrangement has major limitations in the use of the probe and with regard to the images obtained. It has therefore been sought to make two-dimensional arrangements in which the transducer elements are arranged as the cells of a lattice, these being square for example. In this case, the number of elementary transducers to be connected is much greater and it is possible to take off, via a lateral access, only the connections for the elements along the edges of the lattice. It is therefore absolutely essential to make contact in the top and bottom planes of the set of transducers, which are, in this case, subdivided into a relatively large number of separate areas. It is therefore necessary to use a connection method which limits the overall size due to the connections themselves, so as not to increase the size of the probe excessively, and which does not disturb, in an excessive manner, the acoustic properties of the transducers and therefore of the probe.

Technologies are known which can be used to obtain a two-dimensional array of electrical connections, for example by reflowing indium balls. These technologies generally use rigid substrates which disturb the acoustic operation of the transducers. Furthermore, the problem of routing the connections to the outside is not solved thereby.

In order to solve these problems, the invention provides a process for manufacturing a multi-element acoustic probe, especially an echograph probe, in which a piezoelectric plate is divided into a set of elementary transducers that are subsequently equipped with connections, principally characterized in that this plate is firstly fixed to one face of a first polymer film, in that this film is drilled at the points where the connections with the said elementary transducers are to be established, by means of an etching process making it possible to attack the polymer film without attacking the piezoelectric plate, in that conducting tracks are deposited on the other face of the polymer film, which conducting tracks will be connected to the elements via the holes thus drilled in the film, and in that the cuts are then made which allow the elementary transducers to be individualized.

Other features and advantages of the invention will appear clearly in the following description, given by way of non-limiting example with regard to the appended figures which represent.

In order to make the connections to the elements of the probe, the process described in the French patent filed by the Applicant Company on 26 Mar., 1991 under No. 91/03622 and published on 2 Oct., 1992 under No. 2,674,682 is applied. This application is illustrated diagrammatically in FIGS. 1 to 4. The piezoelectric ceramic element 101 to which it is desired to connect an electrical circuit is fixed by adhesive bonding onto a polymer film 102 stretched like a drumskin on a frame. A metal mask 103, is deposited on this polymer film, this metal mask being perforated with holes such as 104 at the places where it is desired to produce the contact or contacts.

Figure 1:
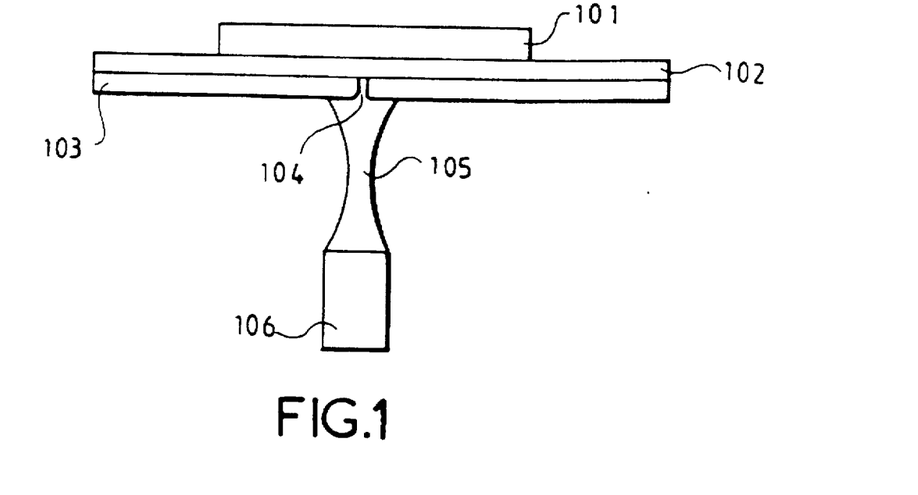
FIGS. 1 to 4, the steps of a connection process according to the known art.

This mask is then illuminated by an ultraviolet beam 105, obtained for example by an excimer laser 106. Through the effect of the ultraviolet radiation, the polymer of which the film 102 is composed is attacked by photoablation and is eroded in the region of the hole. The polymer used for the film and the wavelength of the ultraviolet radiation delivered by the laser are chosen, in a known manner, in order to obtain this photoablation effect.

The special characteristic of this photoablation is that it is selective of the polymer or polymers in question and that it produces no effect on the other materials, in particular the metals such as those of which the mask 103 is composed or the metallization deposited on the ceramic 101 in order to be able to excite the latter.

Figure 2:
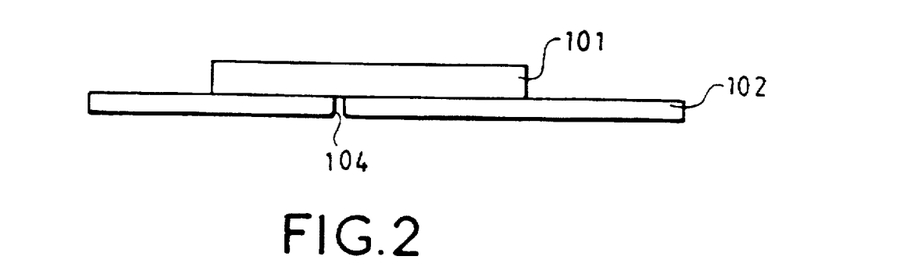

As a result, when the hole is drilled until reaching the level of the ceramic element 101, the action of the ultraviolet radiation stops and the mask 103 can then be removed. In this way, as shown in FIG. 2, a metallized piezoelectric ceramic element 101 adhesively bonded to the polymer film 102 is obtained, which polymer film 102 is obtained, which polymer film includes at least one hole 104 at the place desired for the contact.

This photoablation machining process may be replaced by etching using a plasma, known by the name RIE (Reactive Ion Etching) in which the plasma is obtained by an electrical discharge in an oxygen-based gas mixture. In this process, the etching is also selective and attacks only the organic materials such as the polymers.

Figure 3:
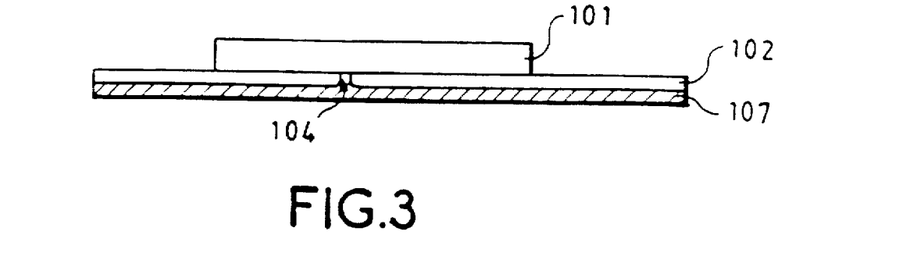

In order to obtain the contacts, a metal layer 107, shown in FIG. 3, is next deposited on the film 102, which metal layer metallizes the hole 104 and covers the surface of the film 102 opposite that to which the ceramic 101 is fixed. This metallization is performed using a known process, for example chemical precipitation or vacuum evaporation.

Figure 4:
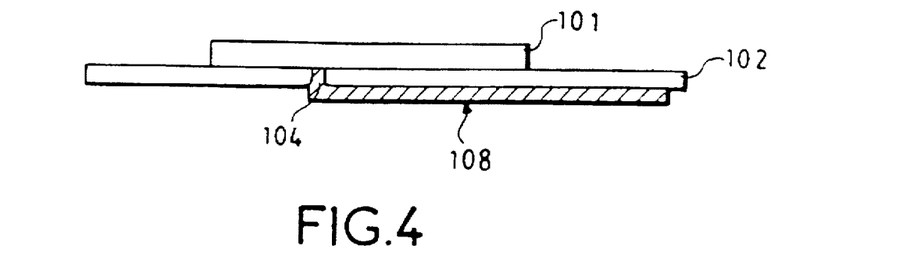

Finally, in a last step, this layer 107 is etched, as shown in FIG. 4, so as to obtain at least one track 108 leaving from the hole 104, via which it is in contact with the ceramic 101, and going on towards the periphery of the film 102 where this track can be connected, for example to a pin of a connector.

Figure 5:
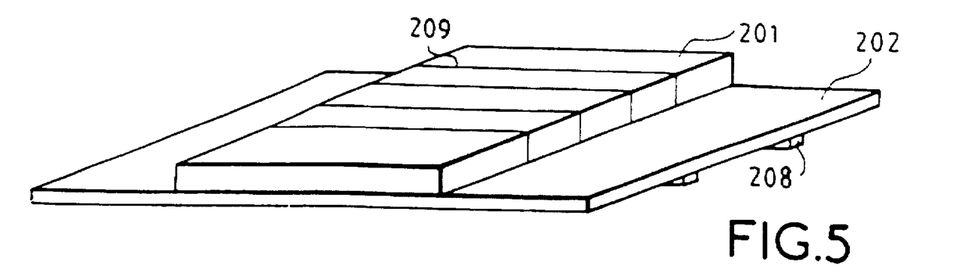
FIGS. 5 to 7, the steps of a first embodiment of a probe obtained by the process according to the invention.
Figure 6:
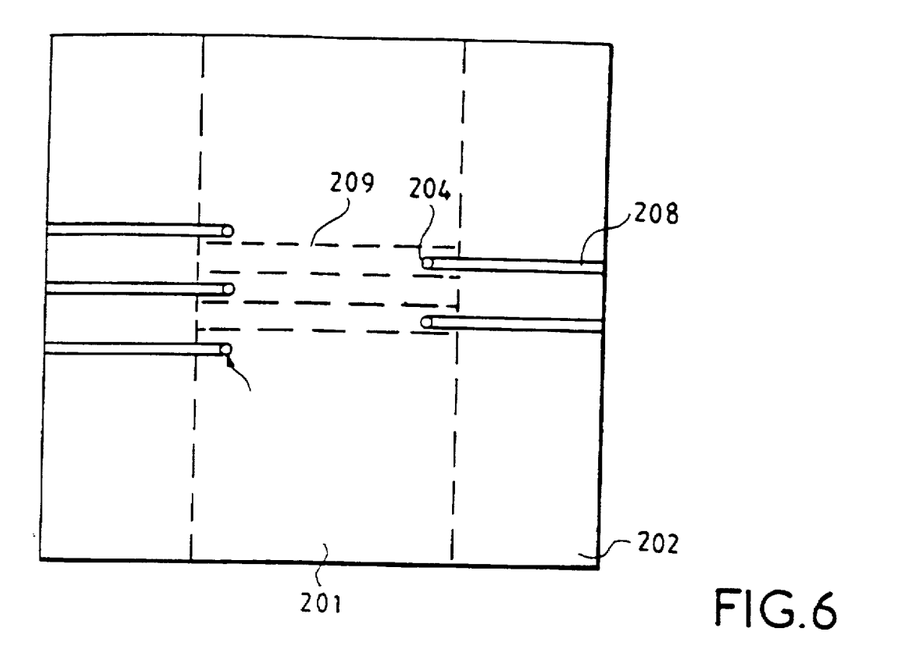
Figure 7:
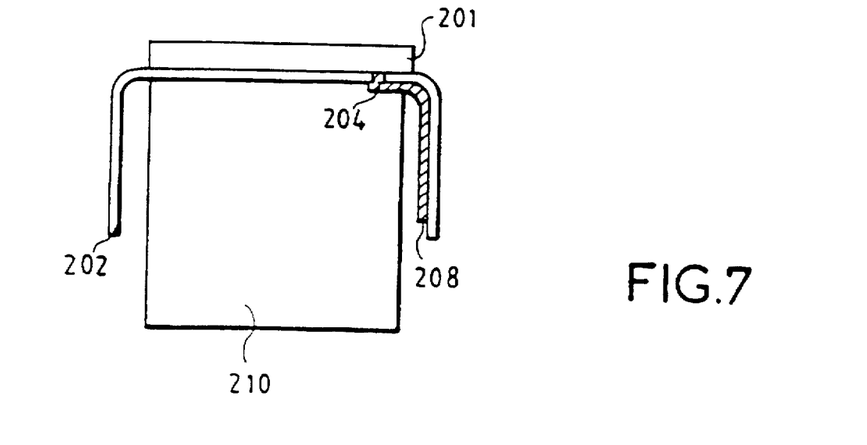
Figure 8:
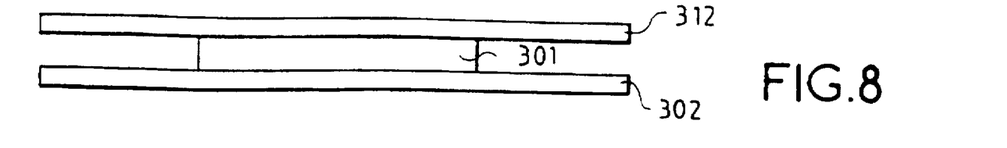
FIGS. 8 to 12, the steps of a second embodiment.
Figure 9:
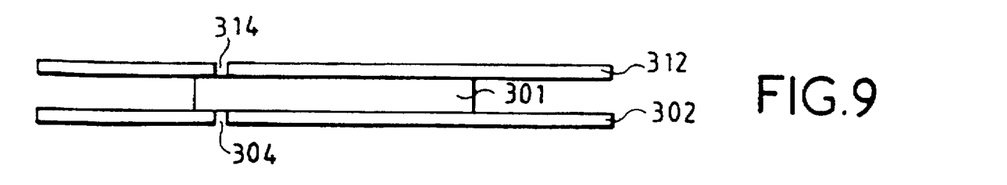
Figure 10:
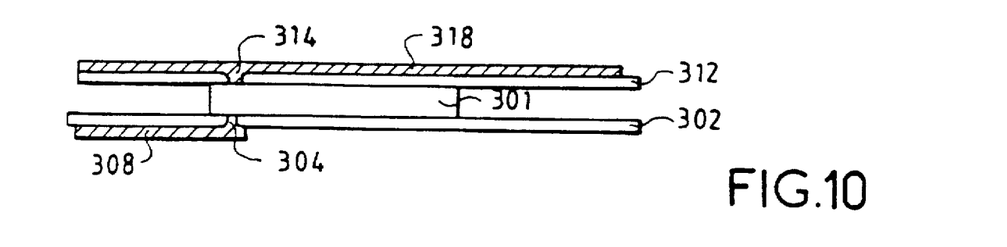
Figure 11:
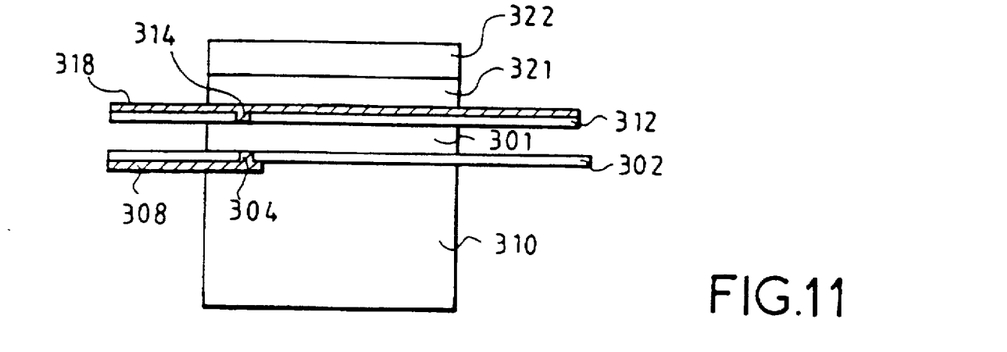

In a first embodiment of the invention, as shown in FIGS. 5 to 7, a multi-element acoustic probe forming a one-dimensional array is manufactured. In this one-dimensional array, the metallized piezoelectric ceramic plate 201 consists of a set of substantially rectangular elements aligned one beside another and formed by cuts in this plate according to the saw kerfs 209 perpendicular to the length of the plate. One or more acoustic matching plates, of the quarter-wave type for example, may be furthermore possibly fixed, for example by adhesive bonding, to the surface of this piezoelectric plate and the sandwich thus obtained may be cut by such saw kerfs.

This array is adhesively bonded to a polymer film 202, preferably before sawing the kerfs 209, and holes 204 are drilled, one per element, using the technique described hereinabove. Next, the metal film is deposited on the bottom surface of the polymer film 202 and then the tracks 208 are etched, these tracks being joined to the plated-through holes 204 during this process of depositing the metal film. In the example described, the holes 204 and the corresponding tracks 208 are placed, from one element to the next, alternately near one of the edges of the ceramic 201 and near the other edge of the latter. In this way, both the holes and the tracks are separated from one another, something which allows the connections to be made more easily and crosstalk between elements to be limited.

In a final step, the film 202 is adhesively bonded by its bottom face to an acoustic support or backing 210 of the transducer. The polymer film may then be folded down towards the base of this backing with the tracks that it supports so as to be clear of the emitting face of the probe.

It is possible to use the same contacting technique to connect the earths, or neutrals, which are generally taken in common for the set of elementary transducers formed by the elements cut into the piezoelectric plate 201. However, it should be pointed out that the technology used would allow, if required, all the earths of the elementary transducers to be connected independently of each other.

The saw kerfs 209 serving to obtain this cut will preferably be made right at the end, after adhesively bonding to the backing 210, in order to make it easier to handle the whole assembly composed of the plate 201, the film 202 and the connection tracks 208.

In a first variant of this first embodiment, shown in FIGS. 8 to 12, the earthing is carried out by using the technique of the invention.

The ceramic plate 301, the top and bottom faces of which are metallized, isolation being maintained by the absence of metallization on the edge of this plate, is adhesively bonded by its top and bottom faces to two polymer films 302 and 312.

Holes 304 and 314 are then produced in these polymer films using the technique described above. In order to etch these holes, the same mask will advantageously be used for the top face and the bottom face, something which presents no difficulty and which simplifies production.

Once these holes have been produced, the external surface of the films 302 and 312 are then metallized. Next, the metallization covering the film 302 is etched in order to obtain the tracks 308 in the same way as seen earlier. However, the metal layer 318 covering the film 312 is left as it is, thereby defining a continuous earth contact area which is connected to the elements of the plate 310 via the holes 314.

Next, the probe is assembled by adhesively bonding the bottom face of the film 302, comprising the tracks 308, to a support 310 also forming the backing, and then by adhesively bonding, at the top surface of the metallization 318, the matching plates such as 321 and 322. The films 302 and 312, including the tracks and the earth metallization are then folded down towards the base of the probe in order to allow suitable connections to be made.

In a final step, this sandwich is cut by saw kerfs which isolate the elementary transducers of the probe. These saw kerfs are parallel to the plane of section of FIG. 12 and the depth of cut is chosen so as to emerge clearly in the thickness of the support 310, stopping at the level of the dotted line 320. The reason for this is that the tracks 308 are parallel to these kerfs and there is thus no risk of cutting them, even on emerging in the support 310. In order to obtain this cut, a known process may be used, for example cutting using a rotating diamond blade. The metallization 318, which is continuous and is only notched by the kerfs, then makes it possible, in addition to its function of earth connection, to screen the tracks 308 running over the film 302.

Figure 12:
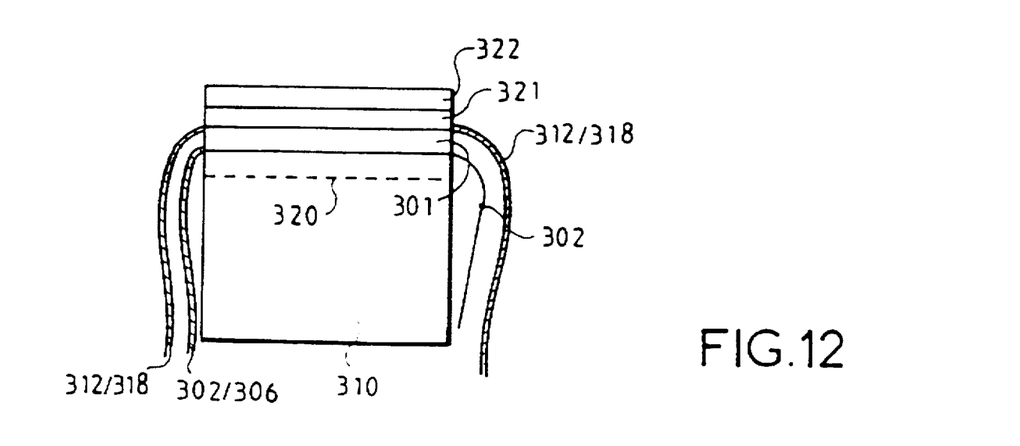

It is then possible to connect microcoaxial cables, providing linkage between the probe and the echograph, to these tracks 308 and to the earth metallization 318. It should be pointed out that this connection may be made equally well on one side of the probe as the other, since the earth metallization 318 is available on both sides. Finally, this probe may be equipped with a lens allowing, in a known manner, focusing in a plane perpendicular to the image plane.

Figure 13:
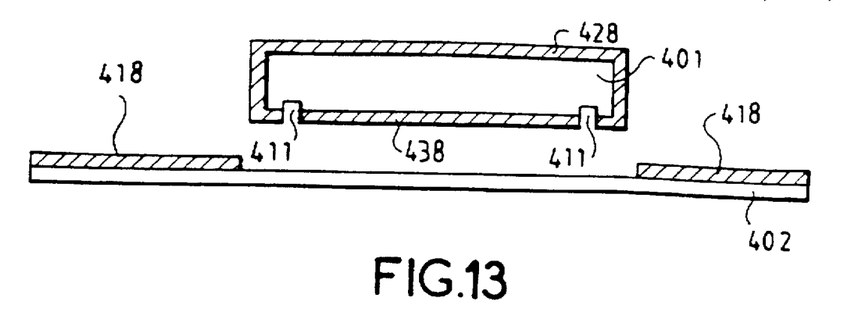
FIGS. 13 to 15, the steps of a third embodiment.
Figure 14:
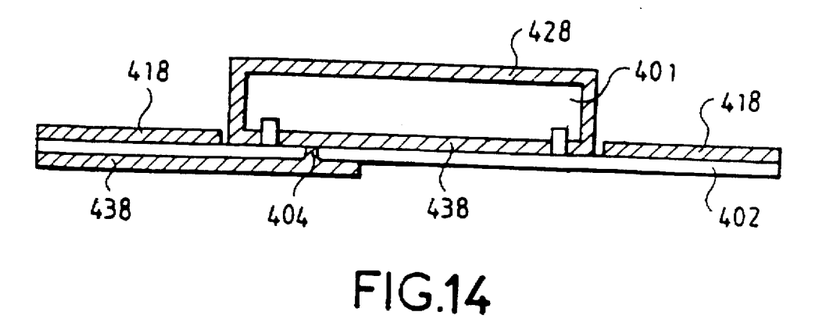
Figure 15:
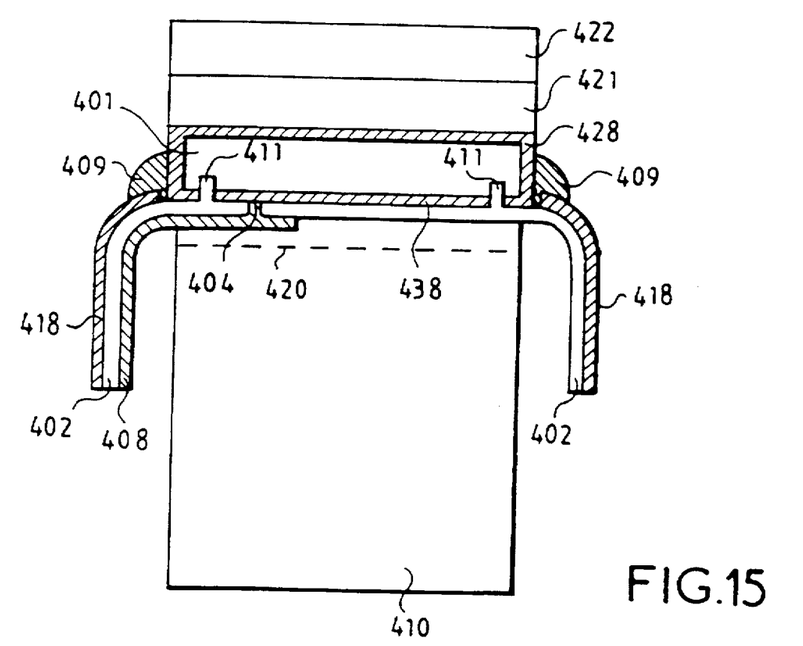

In a second variant of the first embodiment, shown in FIGS. 13 to 15, a single polymer film 402 is used which supports, on its top face, the earth plane 418 and, on its bottom face, the tracks 408 for connection to the elementary transducers cut in the piezoelectric plate 401.

In order to do this, the ceramic plate 401 is completely metallized, or at the very least its two, top and bottom, faces and its two side faces are metallized. Next, this bottom face is notched by two saw kerfs 411 which are located very close to the side faces and which make it possible to isolate a metallized surface 438 carried by this bottom face. This technique is sometimes known as scribing. If the metallization process, for example a chemical metallization process, had resulted in metallization of the ends of the plate 401, it would then be possible, in order for the surface 438 to be well isolated, to use either two saw kerfs perpendicular to the saw kerfs 411 or to cut off the ends of the plate, or else to delay isolation to the moment when finally cutting the elementary transducer elements cut into the plate 401 by cutting these ends.

The polymer film 402 is itself metallized on its top surface, in order to obtain a metallization 418 in which an opening has been made corresponding to the dimensions of the plate 401. This opening may be obtained either during metallization, by effecting a spared area by means of a known process, a mask for example, or a soluble varnish, or after metallization, for example by means of a known photolithographic process.

The plate 401 is then adhesively bonded to the top surface of the film 402 by its face including the saw kerfs 411 and at the place of the spared area effected in the metallization 418.

Next, the process continues, in the manner described above, with the opening of the holes 404, then with the metallization of the bottom surface of the film 402 and with the etching of the tracks 408 which are then connected via the holes 404 to the bottom metallization 438 of the plate 401.

Up to now, the contact with the part 428 of the metallization, which surrounds the plate 401 in order to form the earth electrode, is not in contact with the metallization 418, except may be imperfectly in the region of the edges of the spared area in which this plate 401 is placed.

In the next step, the film 402 is adhesively bonded to the backing support 410, then, possibly, this plate is adhesively bonded to matching plates such as 421 and 422 and, finally, the film 402 is folded down towards the base of the support 410.

Then, in order to achieve earthing, two beads 409 of conductive adhesive are deposited along the metallized lateral faces of the plate 401, these beads extending on one side onto the metallization 418 and on the other side onto the lateral edge of the part 428 of the metallization covering the plate 401.

The process is then completed by cutting the elementary transducers of the probe by means of saw kerfs parallel to the plane of the figure, which kerfs may go down as far as the level of the dotted line 420 in the support 410.

The invention allows a second embodiment, in which the probe is formed by a two-dimensional array of elementary transducers allowing focusing and/or orientation in all space. In fact, a symmetrical twodimensional array, in which the elementary transducers have the shape of squares distributed in the same subdivision in two perpendicular directions X and Y, makes it possible to focus and off-aim the acoustic signal in any direction in space. Such a device, which we will call, for example, a 2D device, therefore includes N×N elementary transducers which have to be able to be connected individually to the members for electronically processing the signal.

Figure 16:
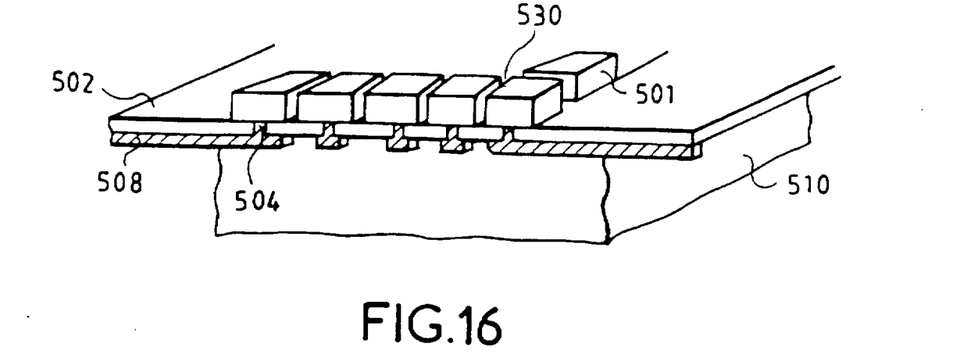
FIGS. 16 to 18, some of the steps of a fourth embodiment.
Figure 17:
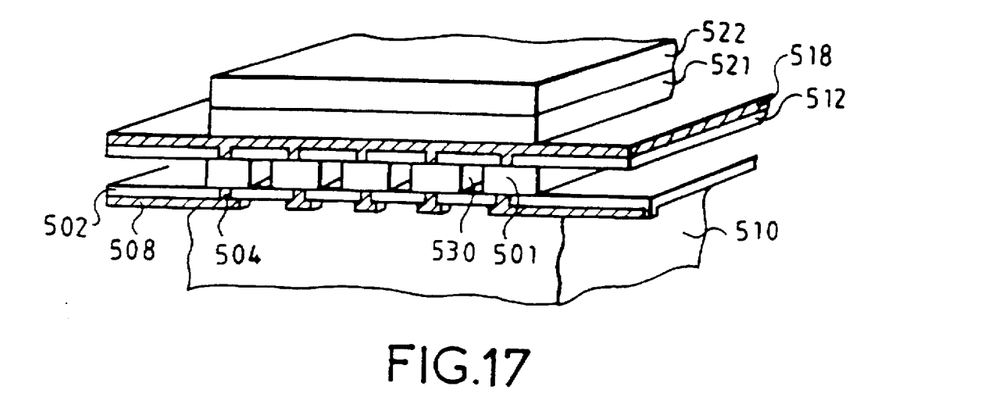
Figure 18:
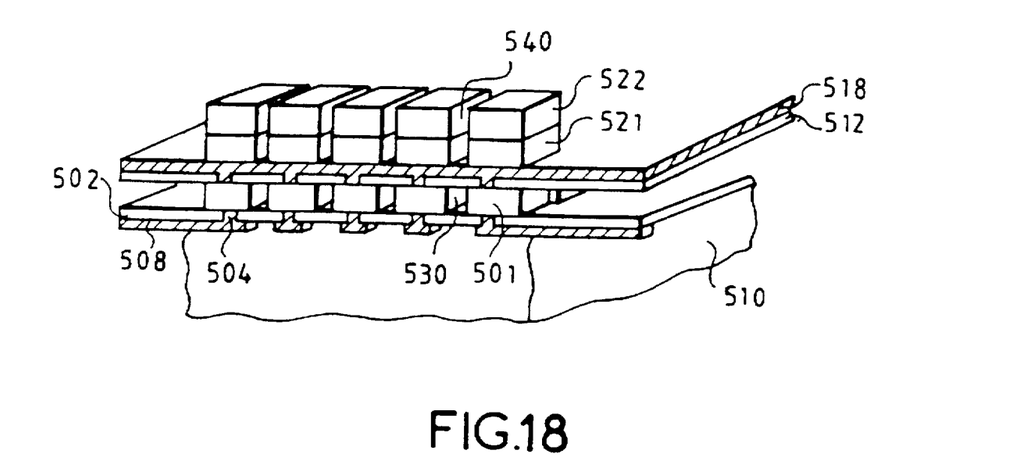

In a first variant, shown in FIGS. 16 to 18, the starting point is a piezoelectric ceramic plate 501 which is adhesively bonded to a polymer film 502 in which the holes 504 have been produced using the process described earlier. A set of tracks 508 is then connected to the metallizations of this piezoelectric plate via the holes 504. Next, this film is adhesively bonded to a backing support 510 and then the plate 501 is cut into a set of perpendicular grooves 530 delimiting square elementary transducers forming an N×N array. The tracks 508, which may have any design, are designed so as to be respectively connected to each of the elementary transducers thus obtained. The plate 501 is cut by means of a known process, for example a very thin diamond blade, but care must be taken that this cut does not completely shear the polymer film 502, so as not to risk cutting the tracks 508. This technique is tricky but it is not outside the scope of cutting normally used in industry.

Next, a second polymer film 512 is adhesively bonded to the top face of the elementary transducers thus separated, in which polymer film are drilled, using the process described earlier, holes which emerge on the top metallizations of the transducer elements cut into the plate 501. Next, the top surface of this film 512 is metallized with a metal coating 518 which is electrically connected to the elementary transducers of the plate 501 via the holes drilled beforehand in the film 512.

There is then a choice either of leaving this metal layer 518 intact, in order to have an earth plane common to all the elementary transducers, or to delineate an array of tracks each connected to one of these elementary transducers, for the case in which it would be necessary to have separate earth contacts, for example because of the electronic processing circuits. In this case, it is possible to use the same design of the array of tracks as that used for the tracks 508.

Next, matching plates such as 521 and 522 are adhesively bonded to this metallization 518 and, in order to avoid acoustic coupling of the elementary transducers between themselves via these matching layers, grooves 540, corresponding to the grooves 530 made in the plate 501, are cut into these matching layers. A first method for making this cut consists in using, as for the plate 501, a diamond saw.

However, as in this case the metallization 518 is directly in contact with the bottom face of the plate 521, it is necessary to stop this cut at a short distance from the bottom face of this plate 521 in order not to notch this very thin metallization. Unfortunately, this method does not get rid of the acoustic coupling between the elementary transducers, which coupling is all the greater the higher generally the acoustic impedance of the plate 521.

Another solution consists, when the matching plates 521 and 522 are manufactured with a composite material using a polymer matrix, this being generally the case, in using one of the techniques described earlier for etching the films 502 and 512, for example laser photoablation. In fact, it has been possible to carry out such machining on thicknesses which may be as high as several millimetres, which is the case for the matching plates generally used. As was seen earlier, the effect of these processes stops immediately the metal layer 518 is reached, and the pieces of matching plate corresponding to the pieces of the piezoelectric plate 501 are then well separated, without this metal earth layer 518 being attacked.

As in the case of the one-dimensional array, the probe thus obtained may be coated, if necessary, with an acoustic lens or with a protective membrane. It is also possible to use a set of microcoaxial cables in order to link this two-dimensional network to the circuits for processing the signals delivered by the probe.

Figure 19:
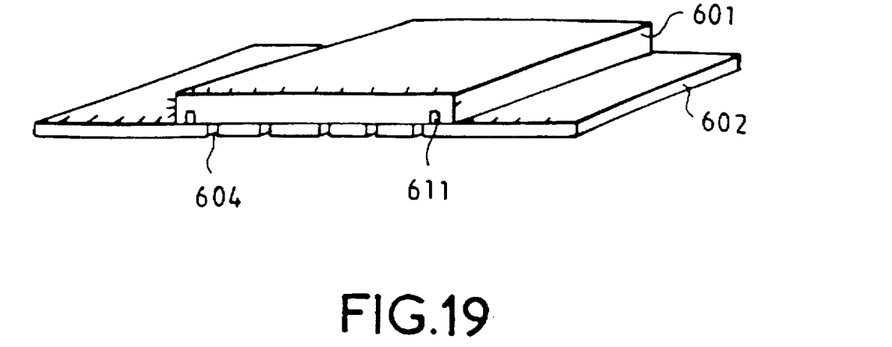
FIGS. 19 and 20, some of the steps of a fifth embodiment.
Figure 20:
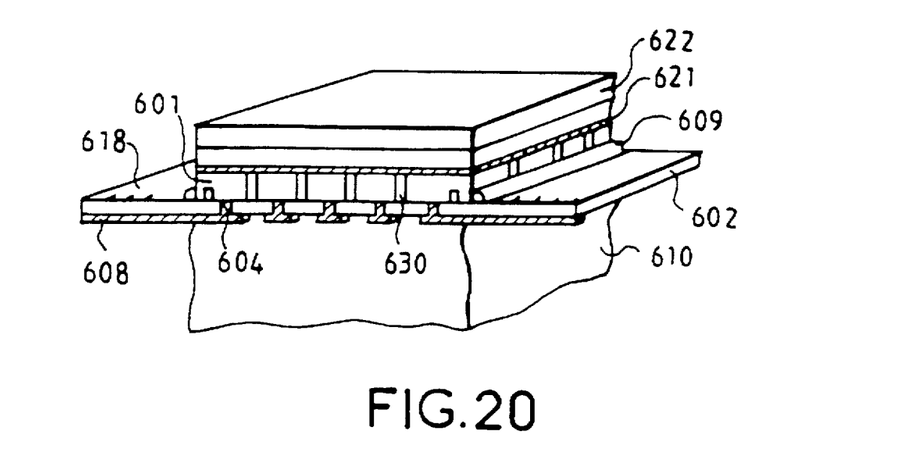

An embodiment variant for taking up the earth circuits, similar to that in FIGS. 13 to 15, is shown in FIGS. 19 and 20.

In this variant, a piezoelectric plate 601 metallized on its four faces, is used, delineating the bottom face by saw kerfs 611. This plate 601 is then adhesively bonded to a polymer film 602 metallized on its bottom and top faces, and on which film a free space with the dimensions of the plate 601 has been left in the metallization of the top face.

Using the process already described, the holes 604 and the tracks 608 on the bottom face of the film 602 are then formed and the whole assembly is adhesively bonded to a support 610.

Next, the grooves 630, which make it possible to delineate the elementary transducers, are cut and matching plates such as 621 and 622 are adhesively bonded to the surface of these elements.

However, in this case, the bottom surface of the matching plate 621 includes a metallization which comes into contact with the top metallization of the elements delineated in the plate 601. In order therefore to make the earth connection, a bead 609 of conductive adhesive is used which links the metallization 618 to the metallization of the lateral faces of the elements of the plate 601. Since this metallization of the lateral faces is continuous with that of the top surface of the lateral elements of this plate, these themselves being in contact with the metallization of the bottom face of the matching plate 621, continuity in the earthing of all the elements cut into the plate 601 is well established.

There then only remains to cut these matching plates 621 and 622 into the same pattern as that into which the plate 601 was cut.

Figure 21:
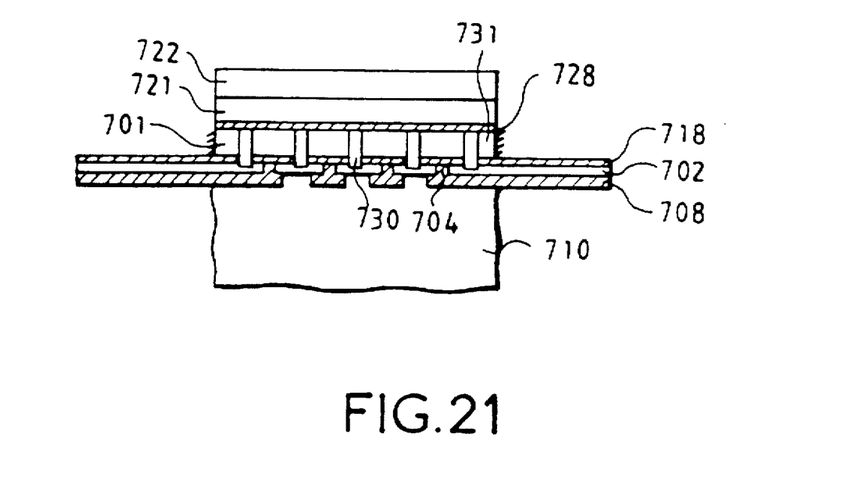
FIG. 21, a sectional view of a probe according to a variant of the fifth embodiment.

In a subvariant of this variant, shown in FIG. 21, a polymer film 702 which includes a continuous top metallization 718 having no spared area is used for adhesively bonding the piezoelectric plate 701. In order then to isolate the earth of that part of the metallization 718 connected to the connections 708 via the holes 704, lateral elements 731, which may be called baffles, are spared when cutting the plate 701, these lateral elements being isolated from the live points corresponding to the connections 708 by providing neither a hole nor a corresponding connection. These baffles 731 are preferably of small size so as not to waste the working area, but if necessary they could be of the same size as the elementary transducers in order to simplify the machining operations.

Thus, the earthing, which is made by the bottom metallization 728 of the plate 721, is therefore continuous with the metallization of the lateral faces of the plate 701, these lateral faces being those of the baffles 731 and then continuous with the metallization 718 of the top face of the film 702. The parts of this metallization 718 lying beneath the elementary transducers are isolated from the earth by the grooves 730 which emerge in the thickness of the film 702.

Figure 22:
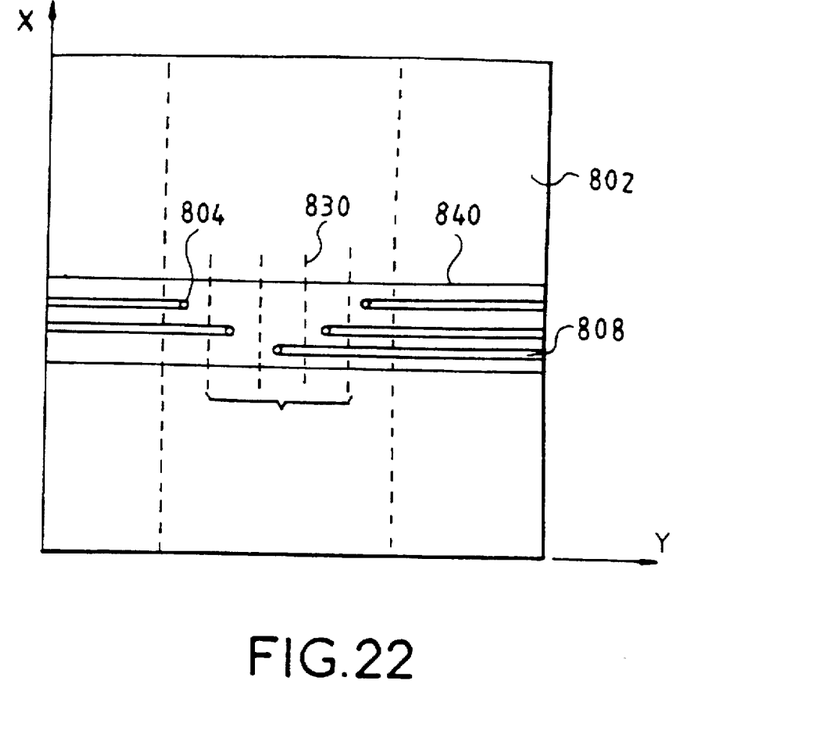
FIGS. 22 and 23, views from below of a probe according to a sixth embodiment.
Figure 23:
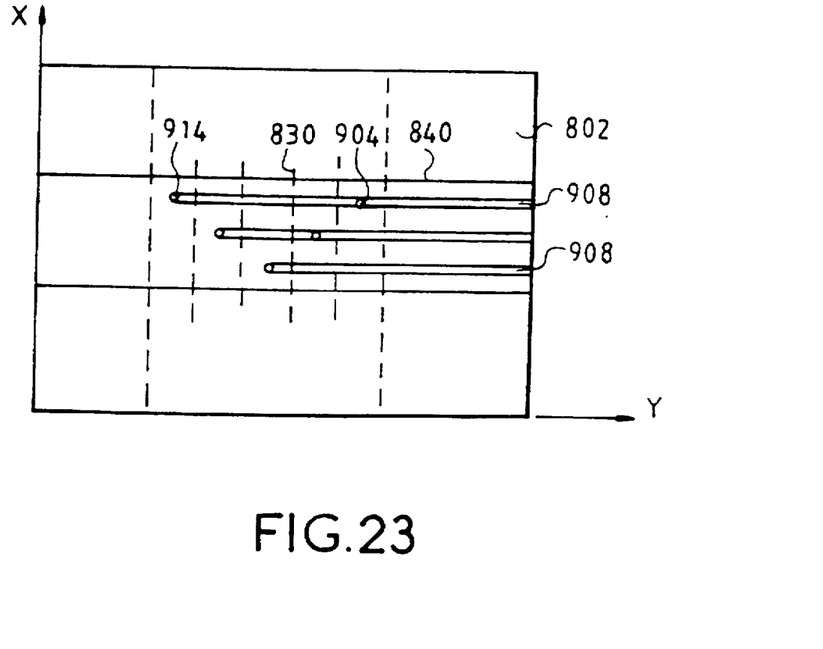

In a final embodiment, represented in two subvariants in FIGS. 22 and 23, an array of rectangular elementary transducers is produced which is therefore asymmetric, having dimensions of N×n. This array, which may be called, for example, a 1.5 D array, therefore has coarser subdivision in one direction, defined by the X axis in the figure. This type of array may be of use in cases where it is not necessary to have the same resolution in both directions, or when it is not necessary to obtain electronic scanning in each direction and when, for example, a single electronic focusing, possibly assisted by a lens, along the X axis may suffice.

The reason for this is that, in this case if the topology of the tracks 808 deposited on the polymer film 802, seen in FIGS. 22 and 23 from underneath, is taken as having a configuration where these tracks remain parallel to each other and to the Y axis, that is to say perpendicular to the X axis, it is then possible to allow the kerfs 840, which determine the coarse subdivision along the X axis, to emerge on the outside of the bottom surface of the film 802, penetrating to a greater or lesser depth into the backing support on which this film has been adhesively bonded. The reason for this is that the length of the elementary transducers along the X axis is large enough to allow such a configuration to be achieved, with tracks and spaces between tracks wide enough for the saw kerf 840 to emerge without the risk of cutting these tracks.

Thus, compared to the previous embodiment, it will therefore be possible to make the cuts 840 only at the end of the process, when the matching plates are in place, through the entire thickness of the sandwich going from the outer matching plate right to the surface of the backing support.

The difference between the two variants of FIGS. 22 and 23 stems from the fact that, in the variant of FIG. 23, the purpose is essentially to achieve electronic focusing in a plane parallel to the X axis, without off-aiming the acoustic beam. Under these conditions, the processing to be applied to the signals from the elementary transducers symmetrical with respect to a central axis parallel to the X axis is identical. It is therefore not necessary to connect them separately to processing means, and it is therefore possible to use a single track 908 joined to two holes 904 and 914 making it possible to connect this track to the symmetrical elements. Of course, when there is an odd number of elements, the central element has only a single connection. In this case, the number of connections to be obtained is substantially divided by two, thereby further facilitating the production of these tracks and the emergence of the saw kerf 840 in the backing support.

We claim:

1. A process for manufacturing a multi-element acoustic probe, comprising the steps of:
    a) dividing a piezoelectric plate having top, bottom and lateral faces into a set of elementary transducer elements;
    b) depositing a conducting layer on the top, bottom, and at least two lateral faces of the plate;
    c) substantially isolating the bottom face of the plate by cutting a line through the conducting layer near the edges of the bottom face of the plate;
    d) depositing a conducting layer on a first face of a polymer film having first and second faces except for a space corresponding to the bottom face of the plate;
    e) fixing the bottom face of the plate to the space on the first face of the film without the conducting layer;
    f) depositing at lest one bead of conducting adhesive on the conducting layer on the first face of the film thereby providing electrical linkage between the conducting layer and at least one lateral face of the plate for the purpose of making an earth connection;
    g) drilling holes in the film by means of an etching process at points where connections to the elementary transducer elements are to be established;
    h) depositing conducting tracks on the second face of the film so that the tracks connect to the elementary transducer elements via the holes in the film; and
    i) cutting the piezoelectric plate to complete formation of the elementary transducer elements.

2. A process for manufacturing a multi-element acoustic probe, comprising the steps of:
    a) dividing a piezoelectric plate having top and bottom faces into a set of elementary transducer elements;
    b) fixing the bottom face of the plate to a first face of a first polymer film having first and second faces;
    c) fixing a first face of a second polymer film having first and second faces to the top face of the piezoelectric plate;
    d) drilling holes in the first film by means of an etching process at points where connections to the elementary transducer elements are to be established;
    e) drilling holes in the second film by means of an etching process at points where connections to the elementary transducer elements are to be established;
    f) depositing conducting tracks on the second face of the first film so that the tracks connect to the elementary transducer elements via the holes in the first film;
    g) depositing conducting material on the second face of the second film to create a conducting layer so that earth connections can be made to the elementary transducer elements via the holes in the second film; and
    h) cutting the piezoelectric plate to complete formation of the elementary transducer elements.

3. A process according to claim 1 wherein the step of depositing conducting tracks further comprises the steps of depositing a conducting metal layer on the second face of the first film so that the conducting metal layer metallizing the holes to establish metal contacts to the elementary transducer elements, and then etching the metal layer to obtain the tracks.

4. A process according to claim 2 wherein the step of depositing conducting tracks further comprises the steps of depositing a conducting metal layer on the second face of the film so that the conducting metal layer metallizing the holes to establish metal contacts to the elementary transducer elements, and then etching the metal layer to obtain the tracks.

5. A process according to claim 1 wherein the step of drilling holes in the films is done by a photoablation process.

6. A process according to claim 2 wherein the step of drilling holes in the film is done by a photoablation process.

7. A process according to claim 1 wherein the step of drilling holes in the films is done by a reactive ion plasma etching process.

8. A process according to claim 2 wherein the step of drilling holes in the film is done by a reactive ion plasma etching process.

9. A process according to claim 1 for obtaining a two-dimensional acoustic probe further comprising the steps of fixing at least one matching plate made of polymer material to the conducting material on the top face of the piezoelectric plate and cutting the matching plate to match the dimensions of the elementary transducer elements.

10. A process according to claim 2 for obtaining a two-dimensional acoustic probe further comprising the steps of fixing at least one matching plate made of polymer material to the conducting material on the second face of the second film and cutting the matching plate to match the dimensions of the elementary transducer elements.

11. A process according to claim 1 for obtaining an asymmetric two-dimensional acoustic probe wherein the step of depositing conducting tracks results in an array of mutually parallel conducting tracks and wherein the step of cutting the piezoelectric plate comprises cutting the plate as well as each layer of film and conducting material by saw kerfs along a longer length of the elementary transducer elements such that the saw kerfs just reach into a support for the acoustic probe.

12. A process according to claim 2 for obtaining an asymmetric multi-element two-dimensional acoustic probe wherein the step of depositing conducting tracks results in an array of mutually parallel conducting tracks and wherein the step of cutting the piezoelectric plate comprises cutting the plate as well as each layer of film and conducting material by saw kerfs along a longer length of the elementary transducer elements such that the saw kerfs just reach into a support for the acoustic probe.

* * * * *